(12) United States Patent
Funamoto

(10) Patent No.: US 9,504,375 B2
(45) Date of Patent: Nov. 29, 2016

(54) LIGHT SOURCE DEVICE AND OBSERVATION APPARATUS

(71) Applicant: Seiko Epson Corporation, Tokyo (JP)

(72) Inventor: Tatsuaki Funamoto, Shiojiri (JP)

(73) Assignee: Seiko Epson Corporation (JP)

( * ) Notice: Subject to any disclaimer, the term of this patent is extended or adjusted under 35 U.S.C. 154(b) by 11 days.

(21) Appl. No.: 14/607,393

(22) Filed: Jan. 28, 2015

(65) Prior Publication Data

US 2015/0208911 A1    Jul. 30, 2015

(30) Foreign Application Priority Data

Jan. 29, 2014  (JP) ................................. 2014-014083

(51) Int. Cl.
*A61B 3/00* (2006.01)
*A61B 3/12* (2006.01)
*A61B 3/14* (2006.01)

(52) U.S. Cl.
CPC ............... *A61B 3/0008* (2013.01); *A61B 3/12* (2013.01); *A61B 3/14* (2013.01)

(58) Field of Classification Search
CPC ...... G02B 26/001; G02B 13/22; G02B 5/28; G02B 5/284; G01J 3/28; G01J 3/2823; G01J 3/45; G01J 3/26; B81B 7/008; B81B 7/02; B81B 5/00; A61B 3/0008; A61B 3/12

USPC .......................... 351/221; 359/577, 578, 519
See application file for complete search history.

(56) References Cited

U.S. PATENT DOCUMENTS 8,063,976 B2 * 11/2011 Kita ....................... G02B 5/284
                                                        348/231.6
2011/0205551 A1 * 8/2011 Saito ........................ G01J 3/26
                                                        359/578

FOREIGN PATENT DOCUMENTS

JP      01-102415 A      4/1989
JP      10-122959 A      5/1998

* cited by examiner

*Primary Examiner* — Euncha Cherry
(74) *Attorney, Agent, or Firm* — Harness, Dickey & Pierce, P.L.C.

(57) ABSTRACT

A light source device includes a light source unit, a light condensing unit that includes a condenser lens which condenses light from the light source unit and a collimator which renders the condensed light into parallel light having a predetermined diameter, and a wavelength variable interference filter which emits light having a wavelength depending on a gap dimension of a pair of reflection films. The predetermined diameter is smaller than a size of a facing region of the wavelength variable interference filter where the pair of reflection films faces each other.

10 Claims, 10 Drawing Sheets

LIGHT SOURCE DEVICE AND OBSERVATION APPARATUS

BACKGROUND

1. Technical Field

The present invention relates to a light source device and an observation apparatus.

2. Related Art

A light source device that selectively extracts light having a predetermined wavelength to emit the extracted light has been known (for example, see JP-A-1-102415).

In JP A-1-102415, the light source device uses a Fabry-Perot variable interference unit (interference filter) in order to extract light having a predetermined wavelength among light rays from a light source. Specifically, in the device described in JP A-1-102415, the light from the light source is rendered into parallel light by a lens, and the parallel light is incident on the interference filter.

In the light source device described in JP A-1-102415, it is possible to reduce a size of the light source device by using the interference filter as compared to a case where other spectroscopic devices such as an acousto-optic tunable filter (AOTF) or a liquid crystal tunable filter (LCTF) is used.

In general, the above-mentioned interference filter causes light to be incident on a region where a pair of reflection films faces each other and emits light having a predetermined wavelength. In the light source device using such an interference filter, in order to suppress a loss in light amount of illumination light, it is conceivable that areas of the reflection films of the interference filter are increased such that the light from the light source is incident on the reflection films.

However, when the areas of the reflection films are increased, the reflection film may be easily bent, and resolution thereof may be degraded.

SUMMARY

An advantage of some aspects of the invention is to provide a light source device and an observation apparatus capable of emitting illumination light having a desired wavelength with high resolution and suppressing a loss in light amount of the illumination light.

According to an aspect of the present invention, there is provided a light source device including: a light source unit; a light condensing unit that condenses light from the light source unit, and renders the condensed light to parallel light having a predetermined diameter; and an interference filter that has a pair of reflection films facing each other, and emits light having a wavelength depending on a gap dimension of the pair of reflection films among the parallel light rays. The predetermined diameter is smaller than a size of a facing region of the interference filter where the pair of reflection films faces each other.

In this case, by using the condensing unit, the light from the light source unit is rendered into the parallel light having the diameter smaller than that of the facing region of the pair of reflection films of the interference filter and the parallel light is incident on the interference filter.

For example, when an aperture having an opening overlapped with an effective region is provided on a light incident side of the interference filter, if parallel light having a diameter greater than that of the effective region is incident on the interference filter, the light incident on a region other than the effective region is blocked by the aperture. That is, some of the condensed light rays are blocked, and, thus, the light amount of the light source device is reduced.

In a plan view viewed in a thickness direction of the reflection films, compared to centers of the reflection films, portions which are largely bent or portions which have non-uniform thicknesses are highly likely to exist in regions near outer peripheries of the reflection films. Accordingly, compared to the centers of the reflection films, variation of the wavelength of the emission light may be severed and the resolution thereof may be deteriorated in the regions near the outer peripheries of the reflection films. Accordingly, when the aperture is not provided, if the light is incident on the entire facing region of the pair of the reflection films, the resolution of the emission light from the interference filter may be degraded.

In contrast, in the light source device of the aspect of the present invention, the light from the light source unit is rendered into the parallel light having the size smaller than that of the facing region where the pair of reflection films faces each other and the parallel light is incident. In this case, since the parallel light is incident on the centers of the reflection films, it is possible to suppress a reduction in utilization efficiency of the light from the light source unit, and it is possible to suppress a loss in the light amount. Further, it is possible to suppress a reduction in resolution of the emission light from the interference filter by causing the parallel light to be incident on the centers of the reflection films while avoiding the outer peripheries of the reflection films.

That is, it is possible to extract light having a predetermined wavelength from the light emitted from the light source unit with high efficiency and high resolution, and to use the extracted light as illumination light.

In the light source device according to the aspect of the present invention, the parallel light may be incident on an effective region in the facing region of the interference filter where a wavelength of emission light falls within a predetermined allowable error range of a target wavelength depending on the gap dimension.

In this case, the predetermined allowable error range refers to a range that is allowable as the error of the wavelength of the light emitted from the light source device, and is appropriately set depending on the purpose.

In this case, the parallel light is incident within the region of the facing region of the interference filter where the wavelength of the emission light falls within the predetermined allowable error range of the target wavelength. Accordingly, it is possible to more reliably suppress a reduction in resolution of the emission light from the interference filter, and it is possible to output light having a desired target wavelength from the light source device.

In the light source device according to the aspect of the present invention, the predetermined diameter may be equal to or less than 2.5 mm.

In this case, by setting the predetermined diameter to be 2.5 mm or less, a value of a standard deviation representing a variation of the wavelength of the emission light from the interference filter in a surface orthogonal to a traveling direction can be suppressed to be 5 nm or less. Accordingly, when illumination light having a plurality of wavelengths is emitted from the interference filter while changing a dimension between the reflection films of the interference filter, even though the plurality of wavelengths has an interval of 10 nm, the wavelength of the illumination light can be distinguished between target wavelengths closest to each other, and a changing interval of the wavelength can be sufficiently decreased.

Preferably, the light source device according to the aspect of the present invention may further include a retreating unit that retreats the interference filter from an optical path of the parallel light.

In this case, the light source device further includes the retreating unit that retreats the interference filter from a disposing position disposed on the optical path of the parallel light to a retreating position retreated from the optical path. Accordingly, it is possible to retreat the interference filter to the retreating position, and it is possible to easily change the illumination light between dispersed light and undispersed light (that is, light from the light source unit).

The light source device according to the aspect of the present invention may further include a housing that stores the interference filter, and has a window that transmits light incident on the interference filter. The light condensing unit may have a collimator that emits the parallel light, and the collimator may be provided at the window.

In this case, the interference filter is stored within the housing at which the collimator of the light condensing unit is provided. For this reason, it is possible to prevent foreign substances from adhering to the reflection films, and it is possible to protect the interference filter from impacts.

According to another aspect of the present invention, there is provided an observation apparatus including: a light source device that includes a light source unit, a light condensing unit which condenses light from the light source unit and renders the condensed light into parallel light having a predetermined diameter, and an interference filter which has a pair of reflection films facing each other and emits light having a wavelength depending on a gap dimension of the pair of reflection films among the parallel light rays, the predetermined diameter being smaller than a size of a facing region of the interference filter where the pair of reflection films faces each other; an illumination optical system that guides the light emitted from the light source device to illuminate a target; and an observation unit that observes light reflected from the target.

In this case, similarly to the aforementioned light source device, the light from the light source unit is rendered into the parallel light having the diameter smaller than that of the facing region of the pair of reflection films of the interference filter and the parallel light is incident on the interference filter by using the condensing unit.

Accordingly, similarly to the aforementioned light source device, it is possible to extract light having a predetermined wavelength from the light emitted from the light source unit with high efficiency and high resolution, and to use the extracted light as illumination light.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, a light source device and an ocular fundus observation apparatus according to a first embodiment of the present invention will be described with reference to the drawings.

Figure 1:
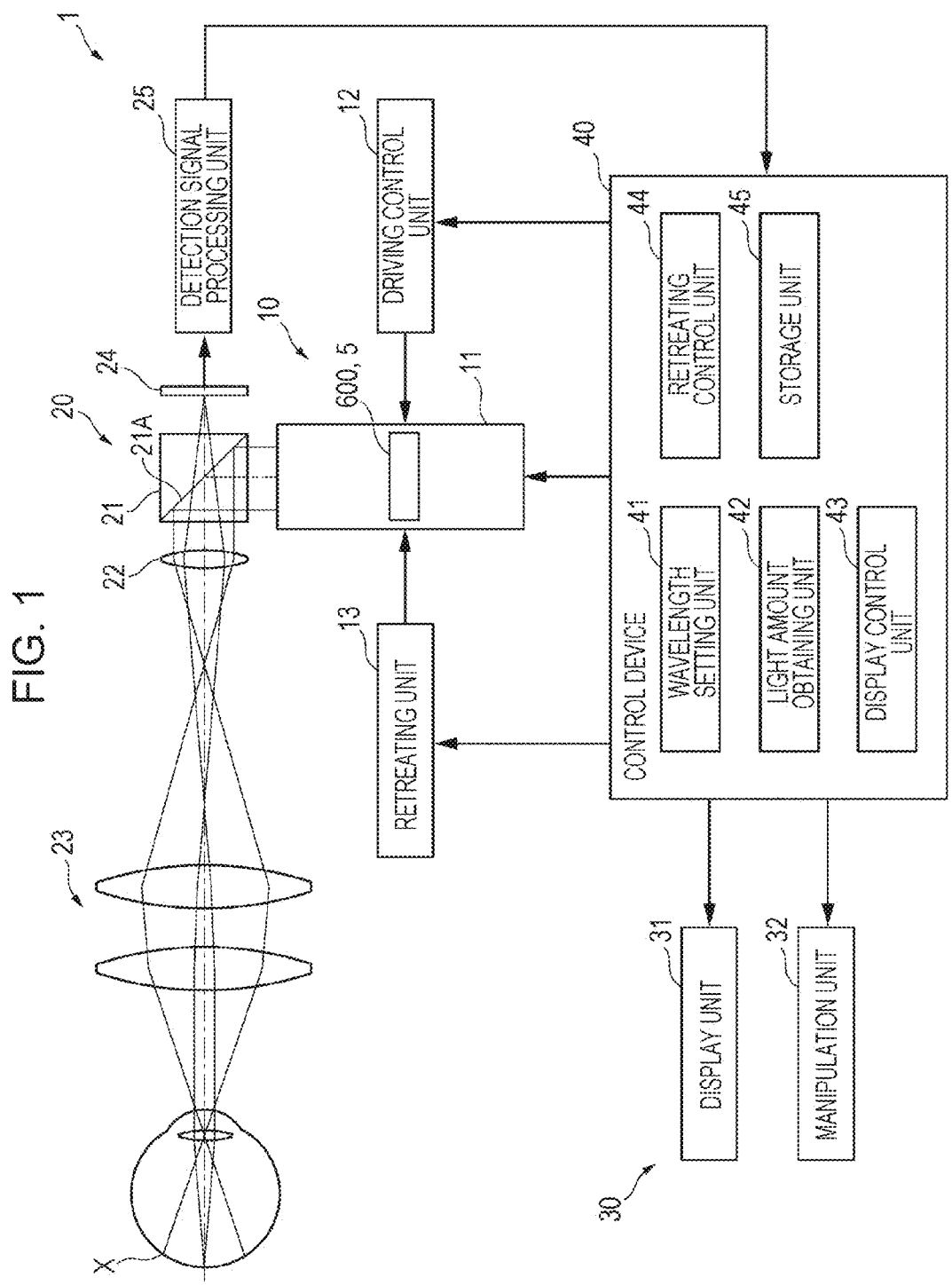
FIG. 1 is a diagram illustrating a schematic configuration of an ocular fundus observation apparatus which is an observation apparatus according to a first embodiment of the present invention.

FIG. 1 is a diagram illustrating a schematic configuration of an ocular fundus observation apparatus 1 of the present embodiment.

As illustrated in FIG. 1, the ocular fundus observation apparatus 1 of the present embodiment includes a light source device 10, an optical device 20, an input and output device 30, and a control device 40.

The ocular fundus observation apparatus 1 is a device that applies light from the light source device 10 to an ocular fundus, and captures observation light which is a reflected light from the ocular fundus to obtain an ocular fundus image.

Configuration of Light Source Device

The light source device 10 includes a light source unit 11 that includes an optical filter device 600 configured such that a wavelength variable interference filter 5 is stored in a housing 610, a driving control unit 12, and a retreating unit 13. As will be described below, the wavelength variable interference filter 5 is an optical element that selectively extracts light having a predetermined wavelength from light incident on an effective region having a predetermined effective diameter.

The light source unit 11 causes light from a light source section 111 to be described below to be incident on the wavelength variable interference filter 5, and emits extracted light having the predetermined wavelength as illumination light.

Figure 2:
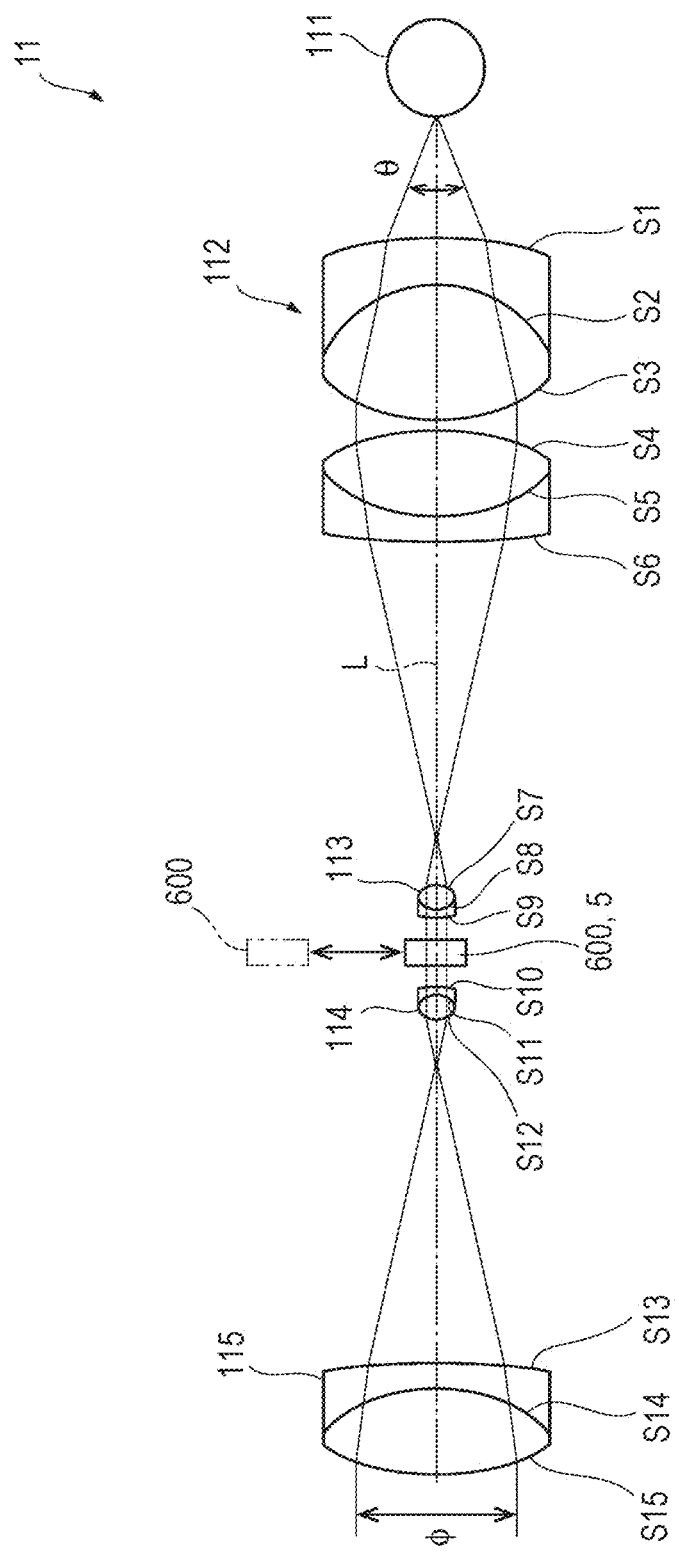
FIG. 2 is a diagram showing a schematic configuration of a light source unit of the first embodiment.

FIG. 2 is a diagram showing a schematic configuration of the light source unit 11.

As illustrated in FIG. 2, the light source unit 11 includes the light source section 111, a condenser lens 112, a collimator 113, a magnifying lens 114, and a collimator 115.

The light source section 111 is a light source that can emit light having a wavelength band used for ocular fundus observation. As the light source section 111, LEDs or various incandescent light sources such as tungsten lamps filled with xenon or halogen may be used. The light source section 111 may appropriately include a reflector in addition to the light source.

The condenser lens 112 condenses light emitted from the light source section 111. As shown in FIG. 2, the condenser lens 112 is a doublet lens having a plurality of lens surfaces. In the example shown in FIG. 2, the condenser lens has six lens surfaces S1 to S6 in sequence from the light source section 111.

The collimator 113 renders light condensed to a predetermined diameter by the condenser lens 112 into parallel light, and causes the parallel light to be incident on the wavelength variable interference filter 5. In the present embodiment, similarly to the condenser lens 112, the collimator 113 has a plurality of lens surfaces. In the example shown in FIG. 2, the collimator 113 has three lens surfaces S7 to S9 in sequence from the light source section 111. The condenser lens 112 and the collimator 113 correspond to a light condensing unit of the present invention.

Figure 3:
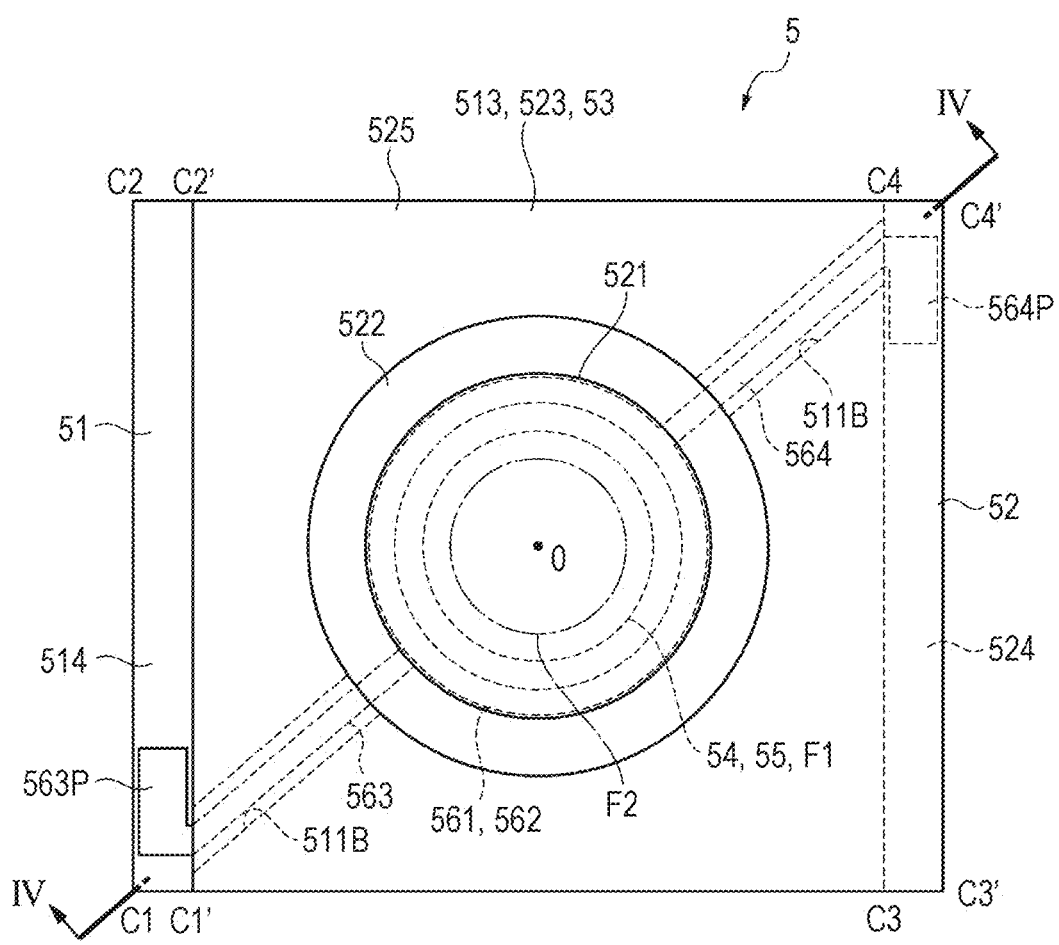
FIG. 3 is a plan view showing a schematic configuration of a wavelength variable interference filter of the first embodiment.

Here, a diameter of light rendered into the parallel light by the collimator 113 is equal to or less than that of an effective region F2 (a region having a size smaller than that of a facing region F1 where a pair of reflection films faces each other, as illustrated in FIG. 3) of the wavelength variable interference filter 5 to be described below (hereinafter, the diameter of the effective region is referred to as an effective diameter).

The magnifying lens 114 receives light having a predetermined wavelength which is emitted from the collimator 113 and is transmitted through the wavelength variable interference filter 5, and magnifies the received light. In the present embodiment, similarly to the condenser lens 112, the magnifying lens 114 has a plurality of lens surfaces. In the example shown in FIG. 2, the magnifying lens 114 has three lens surfaces S10 to S12 in sequence from the light source.

The collimator 115 renders light magnified by the magnifying lens 114 into parallel light. In the present embodiment, similarly to the condenser lens 112, the collimator 115 has a plurality of lens surfaces. In the example shown in FIG. 2, the collimator 115 has three lens surfaces S13 to S15 in sequence from the light source section 111.

In the present embodiment, a case where radii of curvature of the lens surfaces S1 to S15, distances between the lens surfaces, and materials between the lens surfaces are set as shown in Table 1 below is presented as an example.

In a distance field of Table 1, a distance between a lens surface corresponding to each distance field and a lens surface immediately preceding the corresponding lens surface in a traveling direction of light is described. For example, a distance from the lens surface S1 to the lens surface S2 is described in the distance field of the lens surface S2. A distance from the light source section 111 to the lens surface S1 is described in the distance field of the lens surface S1.

In a material field of Table 1, a material of an optical path between a lens surface corresponding to each material field and a lens surface immediately preceding the corresponding lens surface in the traveling direction of light is described. For example, a material between the lens surface S1 and the lens surface S2 is described in the material field of the lens surface S2.

TABLE 1

| Lens Surface | Radius of Curvature | Distance (mm) | Material |
| --- | --- | --- | --- |
| S1 | −41.7 | 14.49291 | — |
| S2 | −13.84 | 5 | N-SF66 |
| S3 | 18.85 | 15.33 | N-BASF64 |
| S4 | −29.97 | 1 | — |

TABLE 1-continued

| Lens Surface | Radius of Curvature | Distance (mm) | Material |
| --- | --- | --- | --- |
| S5 | 18.85 | 9.5 | S-BAH11 |
| S6 | 152.94 | 2.5 | N-SF10 |
| S7 | −4.24 | 38 | — |
| S8 | 2.6 | 2.8 | N-BASF10 |
| S9 | 18.9 | 1 | N-SF10 |
| S10 | −18.9 | 1 | — |
| S11 | −2.6 | 1 | N-SF10 |
| S12 | 4.24 | 2.8 | N-BASF10 |
| S13 | −152.94 | 38 | — |
| S14 | −18.85 | 2.5 | N-SF10 |
| S15 | 27.97 | 9.5 | S-BAH11 |

It is possible to set a capturing angle θ of the light from the light source section 111 to about 36° by setting the condenser lens 112, the collimator 113, the magnifying lens 114 and the collimator 115 which are optical elements as represented in Table 1.

A diameter of light emitted from the collimator 113 can be set to about 2.5 mm, and can be set to be approximately equal to the effective diameter of the wavelength variable interference filter 5 to be described below.

A diameter φ of emission light from the collimator 115, that is, the light source device 10 is set to 18 mm. As described above, it is possible to set the diameter φ of the emission light from the light source device 10 to be greater than that of the effective diameter of the wavelength variable interference filter 5.

Configuration of Wavelength Variable Interference Filter

The wavelength variable interference filter 5 is an example of the optical element of the present invention.

Figure 4:
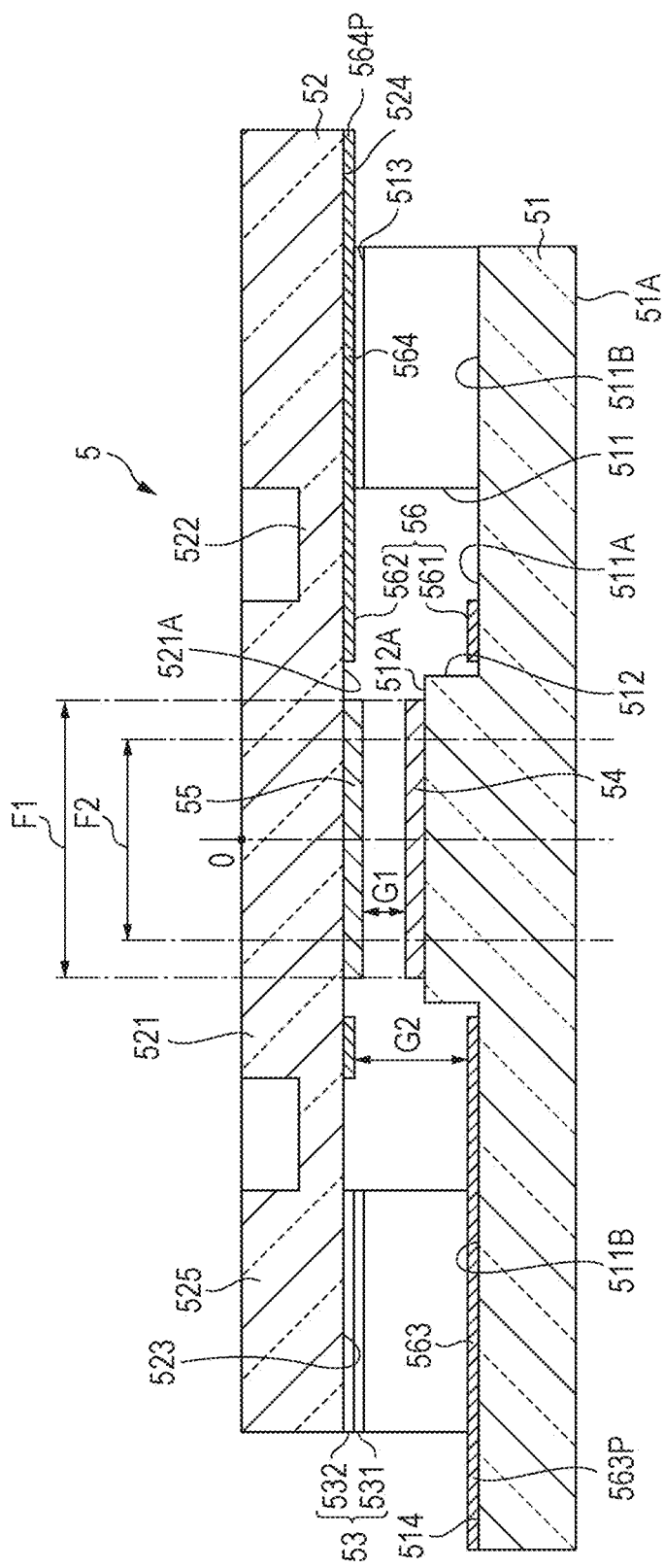
FIG. 4 is a cross-sectional view showing the schematic configuration of the wavelength variable interference filter of the first embodiment.

FIG. 3 is a plan view showing a schematic configuration of the wavelength variable interference filter 5, and FIG. 4 is a cross-sectional view taken along line IV-IV of FIG. 3 to illustrate the schematic configuration of the wavelength variable interference filter 5.

As shown in FIG. 3, the wavelength variable interference filter 5 includes a fixed substrate 51 and a movable substrate 52 that are respectively provided with reflection films. The fixed substrate 51 and the movable substrate 52 are respectively made from, for example, a crystal or various types of glass such as soda glass, crystalline glass, quartz glass, lead glass, potassium glass, borosilicate glass, and non-alkali glass. As illustrated in FIG. 4, the fixed substrate 51 and the movable substrate 52 are integrally formed by being bonded by a bonding film 53 (a first bonding film 531 and a second bonding film 532). Specifically, a first bonding section 513 of the fixed substrate 51 and a second bonding section 523 of the movable substrate 52 are bonded by the bonding film 53 made from a plasma polymerized film containing siloxane as a main component, for example.

In the following description, a plan view viewed in a thickness direction of the fixed substrate 51 and the movable substrate 52, that is, a plan view when the wavelength variable interference filter 5 is viewed in a laminated direction of the fixed substrate 51, the bonding film 53 and the movable substrate 52 is referred to as a filter plan view.

The fixed substrate 51 is a substrate disposed on a light incident side. As illustrated in FIG. 4, a fixed reflection film 54 serving as one of the pair of reflection films of the present invention is formed on the fixed substrate 51. A movable reflection film 55 serving as the other one of the pair of reflection films of the present invention is formed on the movable substrate 52. The fixed reflection film 54 and the movable reflection film 55 are arranged to face each other (hereinafter, a region where the reflection films 54 and 55 face each other is referred to as a facing region F1) with an inter-reflection-film gap G1 formed therebetween.

An electrostatic actuator 56 used to adjust a distance of the inter-reflection-film gap G1 (gap dimension) is provided at the wavelength variable interference filter 5. The electrostatic actuator 56 includes a fixed electrode 561 provided at the fixed substrate 51, and a movable electrode 562 provided at the movable substrate 52, and is provided such that the electrodes 561 and 562 face each other. The fixed electrode 561 and the movable electrode 562 face each other with an inter-electrode gap formed therebetween. Here, the electrodes 561 and 562 may be directly provided on surfaces of the fixed substrate 51 and the movable substrate 52, or may be provided over these substrates with another film member interposed therebetween.

Although it has been described in the present embodiment that the inter-reflection-film gap G1 is formed smaller than the inter-electrode gap, the inter-reflection-film gap G1 may be formed greater than the inter-electrode gap depending on a wavelength band transmitted by the wavelength variable interference filter 5.

In the filter plan view, a side C1-C2 of the fixed substrate 51 protrudes outward from a side C1'-C2' of the movable substrate 52 to form a fixed-side electrical section 514. A side C3'-C4' of the movable substrate 52 protrudes outward from a side C3-C4 of the fixed substrate 51 to form a movable-side electrical section 524.

Configuration of Fixed Substrate

An electrode disposing groove 511 and a reflection film forming section 512 are formed on the fixed substrate 51 through etching. The fixed substrate 51 has a thickness greater than that of the movable substrate 52, and, thus, the fixed substrate 51 is not bent due to electrostatic attraction force when a voltage is applied between the fixed electrode 561 and the movable electrode 562 or internal stress of the fixed electrode 561.

The electrode disposing groove 511 is formed in a ring shape with a plane center point O of the fixed substrate 51 as its center in the filter plan view. The reflection film forming section 512 is formed to protrude toward the movable substrate 52 from a center of the electrode disposing groove 511 in the plan view. A groove bottom surface of the electrode disposing groove 511 is an electrode disposing surface 511A on which the fixed electrode 561 is disposed. A protruding front end surface of the reflection film forming section 512 is a reflection film forming surface 512A.

A connection electrode groove 511B is formed in a region from the electrode disposing groove 511 to the fixed-side electrical section 514 and a region from the electrode disposing groove 511 to the side C3-C4 on the fixed substrate 51. In the present embodiment, the electrode disposing surface 511A, a bottom surface of the connection electrode groove 511B and a surface of the fixed-side electrical section 514 are on the same plane.

The fixed electrode 561 constituting the electrostatic actuator 56 is provided on the electrode disposing surface 511A. More specifically, the fixed electrode 561 is provided in a region of the electrode disposing surface 511A facing the movable electrode 562 of a movable section 521 to be described below. An insulating film for securing insulating properties between the fixed electrode 561 and the movable electrode 562 may be laminated on the fixed electrode 561.

A fixed connection electrode 563 connected to an outer periphery of the fixed electrode 561 is provided on the fixed substrate 51. The fixed connection electrode 563 is formed over the fixed-side electrical section 514 and the connection electrode groove 511B formed from the electrode disposing groove 511 toward the fixed-side electrical section 514. The fixed connection electrode 563 constitutes a fixed electrode pad 563P that is electrically connected to an inner terminal to be described below in the fixed-side electrical section 514.

Although it has been described in the present embodiment that one fixed electrode 561 is provided on the electrode disposing surface 511A, for example, two electrodes may be provided as concentric circles with the plane center point O as its center (double electrode configuration). Alternatively, a transparent electrode may be provided at the fixed reflection film 54, or a connection electrode may be provided over the fixed reflection film 54 and the fixed-side electrical section 514 by using the conductive fixed reflection film 54. In this case, the fixed electrode 561 may be partially cut depending on a position of the connection electrode.

As mentioned above, the reflection film forming section 512 includes a reflection film forming surface 512A that is formed in a substantially cylindrical shape having a diameter smaller than that of the electrode disposing groove 511 to be concentric to the electrode disposing groove 511 and faces the movable substrate 52 of the reflection film forming section 512.

As shown in FIG. 4, the fixed reflection film 54 is formed on the reflection film forming section 512. Examples of the fixed reflection film 54 include a metal film such as an Ag film and an alloy film such as an Ag alloy. For example, a dielectric multilayer film in which a high refraction layer is made of $TiO_2$ and a low refraction layer is made of $SiO_2$ may be used. A reflection film in which a metal film (or an alloy film) is laminated on a dielectric multilayer film, a reflection film in which a dielectric multilayer film is laminated on a metal layer (or an alloy film), or a reflection film in which a single-layer refraction layer ($TiO_2$ or $SiO_2$) and a metal film (or an alloy film) are laminated may be used.

An anti-reflection film may be formed at a position corresponding to the fixed reflection film 54 on a light incident surface (a surface on which the fixed reflection film 54 is not formed) of the fixed substrate 51. The anti-reflection film may be formed by alternately laminating a low refraction index film and a high refraction index film, and, thus, reflectivity of visible light on the surface of the fixed substrate 51 can decrease to increase transmittance.

On the surface of the fixed substrate 51 facing the movable substrate 52, a surface on which the electrode disposing groove 511, the reflection film forming section 512 and the connection electrode groove 511B are not formed constitutes the first bonding section 513. The first bonding film 531 is formed at the first bonding section 513, and the first bonding film 531 is bonded to the second bonding film 532 formed at the movable substrate 52. By doing this, the fixed substrate 51 and the movable substrate 52 are bonded to each other.

Configuration of Movable Substrate

The movable substrate 52 includes the movable section 521 having a circular shape with the plane center point O as its center, and a holding section 522 that is concentric to the movable section 521 and holds the movable section 521.

The movable section 521 is formed to have a thickness greater than that of the holding section 522. The movable section 521 is formed to have a diameter greater than at least a diameter of an outer periphery of the reflection film forming surface 512A in the filter plan view. The movable electrode 562 and the movable reflection film 55 are formed at the movable section 521.

Similarly to the fixed substrate 51, an anti-reflection film may be formed on a surface of the movable section 521 opposite to the fixed substrate 51. The anti-reflection film can be formed by alternately laminating a low refraction index film and a high refraction index film, and, thus, reflectivity of visible light on the surface of the movable substrate 52 can decrease to increase transmittance.

The movable electrode 562 faces the fixed electrode 561 with a gap G2 formed therebetween, and is formed in the same ring shape as that of the fixed electrode 561. The movable electrode 562 and the fixed electrode 561 constitute the electrostatic actuator 56. A movable connection electrode 564 connected to an outer periphery of the movable electrode 562 is provided at the movable substrate 52. The movable connection electrode 564 is formed over the movable-side electrical section 524 and a position facing the connection electrode groove 511B formed to the side C3-C4 of the fixed substrate 51 from the movable section 521, and constitutes a movable electrode pad 564P that is electrically connected to an inner terminal in the movable-side electrical section 524.

The movable reflection film 55 is formed at a center of the movable surface 521A of the movable section 521 to face the fixed reflection film 54 with the gap G1 formed therebetween. As the movable reflection film 55, a reflection film having the same configuration as that of the fixed reflection film 54 is used.

As described above, although it has been described in the present embodiment that the gap G2 has a dimension greater than that of the gap G1, the dimension of the gap G2 is not limited thereto. For example, the dimension of the gap G1 may be greater than that of the gap G2 depending on a wavelength band of the measuring target light as in a case where infrared rays or far-infrared rays are used as measuring target light.

The holding section 522 is a diaphragm surrounding a region around the movable section 521, and is formed to have a thickness smaller than that of the movable section 521. The holding section 522 is more easily bent than the movable section 521, and can displace the movable section 521 toward the fixed substrate 51 by slight electrostatic attraction force. In this case, since the movable section 521 has a thickness greater than that of the holding section 522 to increase stiffness, even when the holding section 522 is pulled toward the fixed substrate 51 by the electrostatic attraction force, a shape of the movable section 521 is not changed. Accordingly, the movable reflection film 55 formed at the movable section 521 is not bent, and, thus, it is possible to constantly maintain the fixed reflection film 54 and the movable reflection film 55 in a parallel state.

Although it has been described in the present embodiment that the holding section 522 has the diaphragm shape, the shape of the holding section is not limited thereto. For example, beam-like holding sections may be arranged at an equiangular space with the plane center point O as its center.

A region of the movable substrate 52 facing the first bonding section 513 is the second bonding section 523. The second bonding film 532 is formed at the second bonding section 523, and the second bonding film 532 is bonded to the first bonding film 531 as stated above. Accordingly, the fixed substrate 51 and the movable substrate 52 are bonded to each other.

In the wavelength variable interference filter 5 having the aforementioned configuration, light from the fixed substrate 51 is incident, and light having a wavelength corresponding to the dimension of the gap G1 set depending on a target wavelength is emitted from the movable substrate 52.

An effective region F2 having a predetermined diameter with the plane center point O as its center is set to the wavelength variable interference filter 5 in the filter plan view. The effective region F2 is a region that can emit light having a wavelength within a predetermined allowable error of the target wavelength.

In the wavelength variable interference filter 5, an aperture having an opening may be formed on a light incident side of the fixed substrate 51 in a position overlapped with the effective region F2 in the filter plan view. Accordingly, it is possible to cause light to be incident on the effective region F2 through the aperture.

Schematic Configuration of Optical Filter Device

Figure 5:
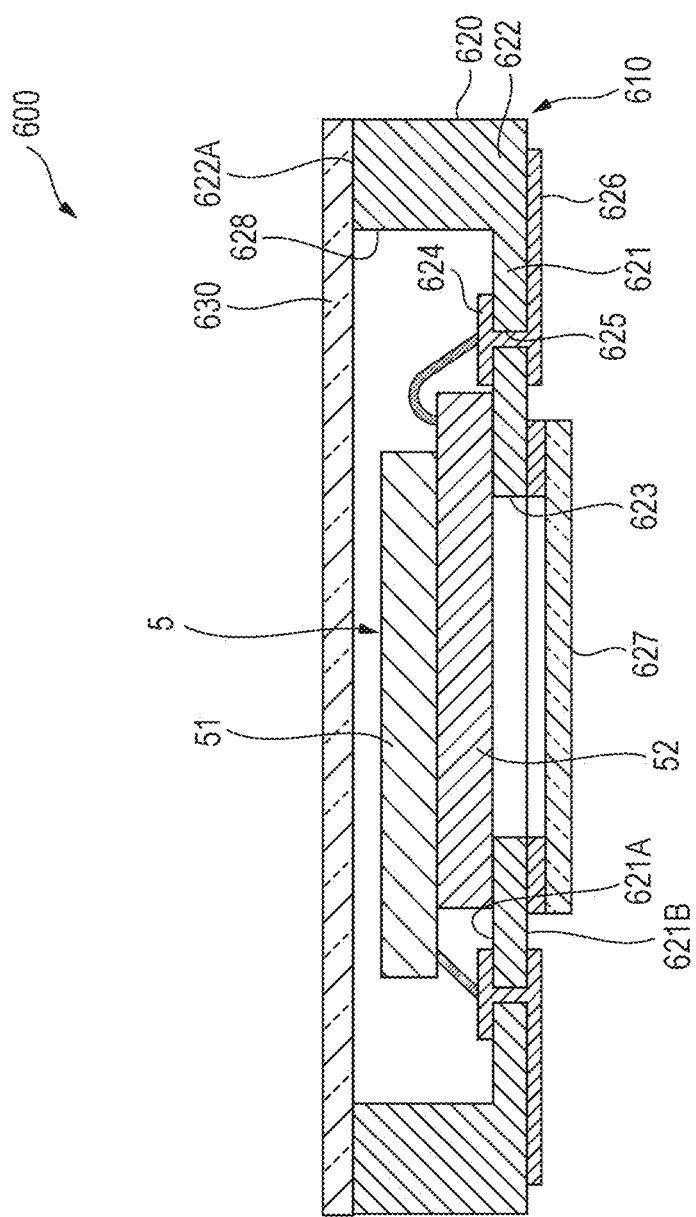
FIG. 5 is a cross-sectional view showing a schematic configuration of an optical filter device of the first embodiment.

FIG. 5 is a cross-sectional view illustrating a schematic configuration of the optical filter device 600.

As illustrated in FIG. 5, the optical filter device 600 includes the housing 610, and the wavelength variable interference filter 5 stored within the housing 610.

As shown in FIG. 5, the housing 610 includes a base 620, and a lid 630. An internal storing space is formed by bonding the base 620 and the lid 630, and the wavelength variable interference filter 5 is stored in the storing space.

Configuration of Base

The base 620 is made of, for example, ceramic. The base 620 includes a pedestal 621, and a sidewall 622.

The pedestal 621 is formed in, for example, a flat plate shape having an external appearance of a rectangular shape in the filter plan view, and the sidewall 622 having a cylindrical shape is erected from an outer periphery of the pedestal 621 toward the lid 630.

The pedestal 621 includes an opening 623 penetrating in a thickness direction. The opening 623 is formed to include a region overlapped with the reflection films 54 and 55 in a plan view when the pedestal 621 is viewed in the thickness direction while the wavelength variable interference filter 5 is stored in the pedestal 621.

A glass member 627 that covers the opening 623 is bonded to a surface (a base outer surface 621B) of the pedestal 621 opposite to the lid 630. The pedestal 621 and the glass member 627 may be bonded by a low-melting-point glass bonding method using a glass frit (glass having a low melting point) which is a piece of glass obtained by melting a glass material at a high temperature and quickly cooling the melted glass material, or an adhering method using epoxy resin. In the present embodiment, the storing space is airtightly maintained in a depressurized state. Accordingly, the pedestal 621 and the glass member 627 are preferably bonded by the low-melting-point glass bonding method.

An inner terminal 624 that is connected to the electrode pads 563P and 564P of the wavelength variable interference filter 5 is formed on an inner surface (a base inner surface 621A) of the pedestal 621 facing the lid 630. The inner terminal 624 and the electrode pads 563P and 564P are connected to each other by using a wire such as an Au wire through wire bonding, for example. Although it has been described in the present embodiment that the inner terminal and the electrode pads are bonded through the wire bonding, the inner terminal and the electrode pads may be bonded using flexible printed circuits (FPC).

A through hole 625 is formed in a position of the pedestal 621 where the inner terminal 624 is formed. The inner terminal 624 is connected to an outer terminal 626 formed on the base outer surface 621B of the pedestal 621 through the through hole 625.

The sidewall 622 is erected from an edge of the pedestal 621, and surrounds a region near the wavelength variable interference filter 5 mounted on the base inner surface 621A. A surface (end surface 622A) of the sidewall 622 facing the lid 630 is a flat surface parallel to the base inner surface 621A, for example. An end of the sidewall 622 close to the lid 630 is open to form a window 628 through which light from the light source section 111 is incident.

The wavelength variable interference filter 5 is fixed to the base 620 by using a fixing material such as an adhesive. In this case, the wavelength variable interference filter 5 may be fixed to the pedestal 621, or may be fixed to the sidewall 622. The fixing material may be provided at a plurality of locations. However, in order to prevent stress of the fixing material from being transferred to the wavelength variable interference filter 5, the wavelength variable interference filter 5 is preferably fixed at one location.

Configuration of Lid

The lid 630 is a transparent material having an external appearance of a rectangular shape in the plan view, and is made of, for example, glass.

As shown in FIG. 5, the lid 630 covers the window 628 which is the opening of the sidewall 622 of the base 620, and is bonded to the sidewall 622. As such a bonding method, a bonding method using glass having a low melting point may be used.

In the filter plan view, an aperture having an opening in a position overlapped with the effective region F2 of the wavelength variable interference filter 5 may be formed in the lid 630. Accordingly, it is possible to cause light to be incident on the effective region F2 of the wavelength variable interference filter 5.

Configuration of Driving Control Unit

The driving control unit 12 applies a driving voltage to the electrostatic actuator 56 of the wavelength variable interference filter 5 under control of the control device 40. Accordingly, electrostatic attraction force is generated between the movable electrode 562 and the fixed electrode 561 of the electrostatic actuator 56 to displace the movable section 521 toward the fixed substrate 51.

Configuration of Retreating Unit

The retreating unit 13 retreats the optical filter device 600 from an optical path L (see FIG. 2). For example, the retreating unit 13 includes a supporting member that supports the optical filter device 600, and a lever is provided at the supporting member. When a user manipulates the lever, the optical filter device 600 can manually be retreated. For example, the retreating unit 13 includes a supporting member that supports the optical filter device 600, a lever that moves the supporting member, and a driving unit such as a motor that moves the supporting member along the lever. The retreating unit may be configured such that the optical filter device 600 is retreated based on a retreating instruction of the user.

Configuration of Optical device

The optical device 20 includes a beam splitter 21, a condenser lens 22, an objective lens 23, a capturing element 24, and a detection signal processing unit 25. Although not shown, the optical device 20 appropriately includes a lens barrel that accommodates the optical elements 21 to 23 therein, or a housing that stores the components 21 to 25.

The beam splitter 21 reflects some light rays incident on a reflection surface 21A, and transmits some light rays to split light incident on the reflection surface 21A.

The condenser lens 22 condenses the incident light.

The objective lens 23 is disposed on an optical path of the optical device 20 to be closest to a target to be observed, and focuses light on an ocular fundus to be observed. In the present embodiment, the objective lens 23 includes, for example, two condenser lenses.

The capturing element 24 receives light which is condensed on the ocular fundus by the objective lens 23 and is reflected from the ocular fundus, and captures an ocular fundus image. The reflection light from the ocular fundus is formed into an image on a capturing surface of the capturing element 24 by the condenser lens 22 and the objective lens 23. The capturing element 24 outputs a detection signal corresponding to the amount of light received from a captured image, that is, pixels of the capturing surface to the detection signal processing unit 25.

The detection signal processing unit 25 amplifies the detection signal (analog signal) input from the capturing element 24, converts the amplified signal into a digital signal, and outputs the converted signal to the control device 40. The detection signal processing unit 25 includes an amplifier that amplifies the detection signal, or an A/D converter that converts an analog signal into a digital signal.

In the optical device 20 having the configuration described above functions as an illumination optical system of the present invention, at least some light rays emitted from the light source device 10 are reflected by the beam splitter 21, are transmitted through the condenser lens 22 and the objective lens 23, and are focused on an ocular fundus X to be observed to illuminate.

Some light rays focused on the ocular fundus X are reflected to be incident on the optical device 20, are transmitted through the beam splitter 21, the condenser lens 22 and the objective lens 23 to form an image in the capturing element 24.

In the present embodiment, although the beam splitter 21 has been used, a perforated mirror may be used instead of the beam splitter 21, and the reflection light from the ocular fundus X may be allowed to pass through an opening of the perforated mirror.

Configuration of Input and Output Device

The input and output device 30 includes a display unit 31 that displays an image, and a manipulation unit 32 that detects manipulation of the user.

The display unit 31 includes various display panels such as a liquid crystal panel, a plasma display panel (PDP), and an organic EL display panel. The display unit 31 displays an ocular fundus observing result by the ocular fundus observation apparatus 1 under control of a display control unit 43. That is, the optical device 20 and the display unit 31 correspond to an observation unit of the present invention.

The manipulation unit 32 includes various units such as a mouse, a keyboard, and a touch panel that can detect the manipulation of the user.

Configuration of Control Device

The control device 40 is configured by combining a CPU and a memory to control the entire operation of the ocular fundus observation apparatus 1. As illustrated in FIG. 1, the control device 40 includes a wavelength setting unit 41, a light amount obtaining unit 42, the display control unit 43, a retreating control unit 44, and a storage unit 45.

V-λ, data representing a relationship between a wavelength of light transmitted through the wavelength variable interference filter 5 and a driving voltage applied to the electrostatic actuator 56 to correspond to the wavelength is stored in the storage unit 45. Various programs and data for controlling the ocular fundus observation apparatus 1 are stored in the storage unit.

The wavelength setting unit 41 sets a target wavelength of light that is extracted by the wavelength variable interference filter 5, and outputs an instruction signal representing that a driving voltage corresponding to the set target wavelength is applied to the electrostatic actuator 56 on the basis of the V-λ data to the driving control unit 12.

Here, the wavelength setting unit 41 sets the target wavelength to a wavelength included in a wavelength band depending on an observation target or an observation method. For example, when the deep retina or the choroid is observed, the wavelength setting unit sets the target wavelength to a wavelength included in a red color wavelength band (for example, 660 nm to 720 nm).

The light amount obtaining unit 42 obtains the amount of light having a target wavelength which is transmitted through the wavelength variable interference filter 5 on the basis of the amount of light obtained by the capturing element 24.

The display control unit 43 generates an observation image on the basis of the amount of light obtained by the light amount obtaining unit 42, and displays the generated observation image on the display unit 31. The display control unit 43 displays various images other than the observation image on the display unit 31.

The retreating control unit 44 controls the retreating unit 13 in response to the manipulation instruction of the user input using the manipulation unit 32 to retreat the optical filter device 600 to a retreating position retreated from a disposing position on the optical path L in the light source device 10. The retreating control unit 44 controls the retreating unit 13 in response to the manipulation instruction of the user to move the optical filter device 600 to the disposing position from the retreating position.

Outline of Operation of Ocular Fundus Observation Apparatus

The ocular fundus observation apparatus 1 having the aforementioned configuration is configured to emit light having a target wavelength selected from a wavelength band depending on the observation target or the observation method from the wavelength variable interference filter 5, focus the light on the ocular fundus X, receive reflection light by the capturing element 24, and capture the observation image.

Specifically, the wavelength setting unit 41 reads a driving voltage corresponding to the target wavelength from the V-λ data stored in the storage unit 45, and outputs an instruction signal representing that the driving voltage is applied to the electrostatic actuator 56 to the driving control unit 12. Accordingly, the driving voltage is applied to the electrostatic actuator 56, and the gap G1 is set to have a dimension corresponding to a measurement wavelength. When the dimension of the gap G1 is set, light having the measurement wavelength is transmitted through the wavelength variable interference filter 5. As the target wavelength, a plurality of wavelengths may be selected from the wavelength bands depending on the observation target or the observation method, or one wavelength may be selected.

The retreating control unit 44 detects a retreating instruction by the user on the basis of the manipulation of the manipulation unit 32 to retreat the optical filter device 600 from the optical path L. When the optical filter device 600 is retreated, the light from the light source unit 11 is focused on the ocular fundus X without being dispersed.

Similarly, the retreating control unit 44 disposes the optical filter device 600 retreated from the optical path L on the optical path L on the basis of the instruction of the user.

EXAMPLE

An example where the ocular fundus observation apparatus 1 having the aforementioned configuration is used will be described below with reference to the drawings.

In this example, a diameter of the facing region F1 where the reflection films 54 and 55 of the wavelength variable interference filter 5 face each other was set to 3.0 mm, and a diameter of the region (light incident region) on which light is incident was set to 2.7 mm. A target wavelength was set to 432 nm.

Wavelengths of illumination light from the light source device 10 in a surface orthogonal to the optical path were measured in regions corresponding to pixels of the capturing element 24.

Figure 6:
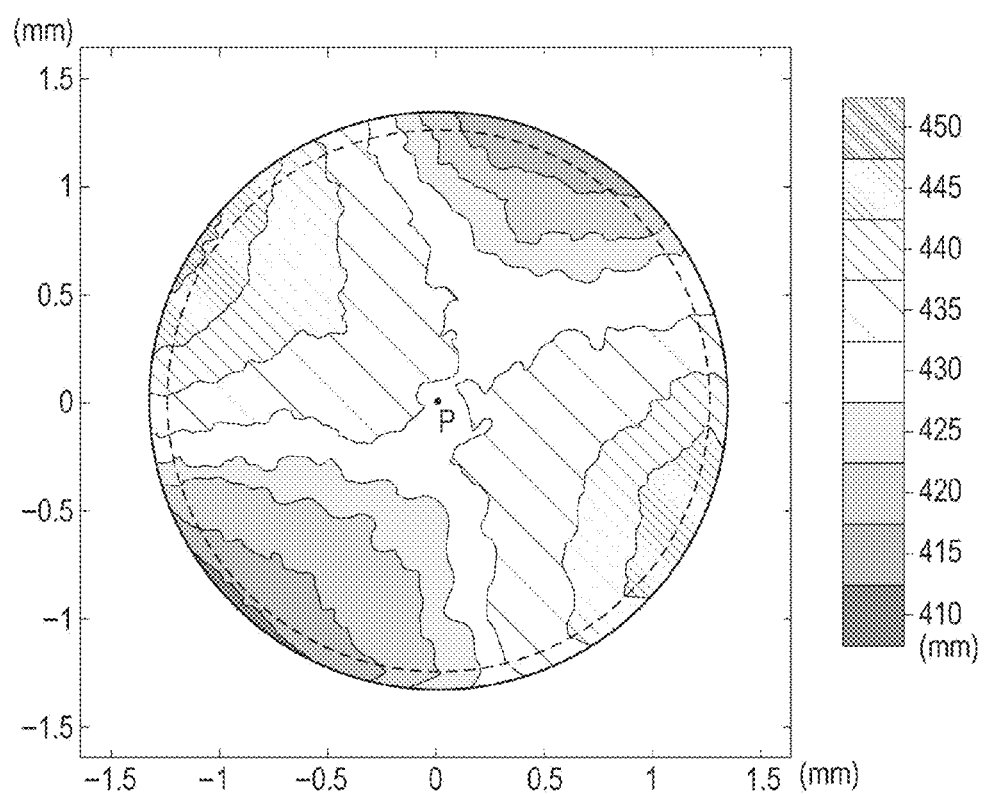
FIG. 6 is a schematic diagram showing an example of an intra-surface distribution of wavelengths of illumination light from a light source device.

FIG. 6 is a diagram illustrating an example of an intrasurface distribution of wavelengths of illumination light from the light source device 10. In FIG. 6, the distribution of wavelengths of the illumination light is shown for wavelength bands with a width of 5 nm, which use nine wavelengths set from 410 nm to 450 nm with an interval of 5 nm as its centers.

As shown in FIG. 6, it can be seen that as it is closer to an outer periphery from a center point P of the light incident region, an error from the target wavelength increases. It can be seen that there is an error of approximately 40 nm between a minimum value and a maximum value near the outer periphery of the light incident region. Accordingly, the light from the light source section 111 is rendered into parallel light smaller than a size of the facing region F1, and the parallel light is incident on the center of the facing region F1. Thus, the light from the light source section 111 is incident on a region smaller than the facing region F1, so that it is possible to suppress a reduction in resolution of the emission light.

Figure 7:
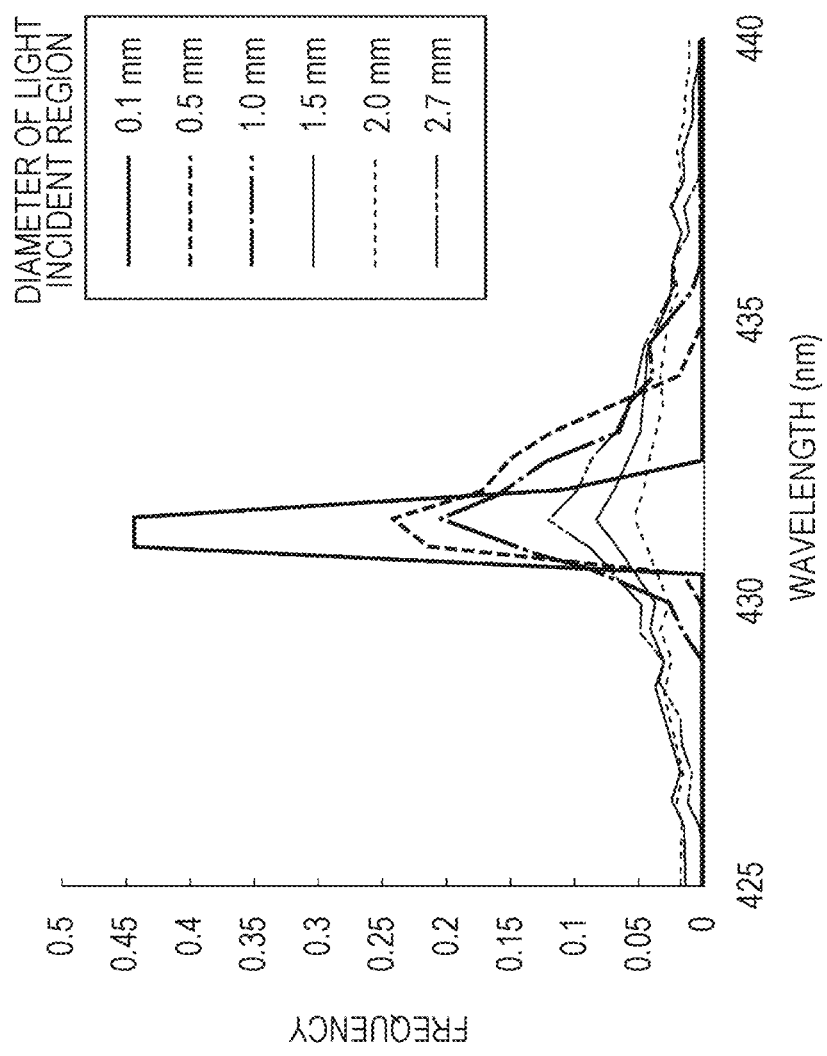
FIG. 7 is a graph showing an example of a frequency distribution of wavelengths of illumination light for diameters in a light incident region.

FIG. 7 is a graph showing a frequency distribution of wavelengths of emission light for each diameter when the center point P of FIG. 6 is used as its center and diameters of the light incident region are respectively set to 0.1 mm, 0.5 mm, 1.0 mm, 1.5 mm, 2.0 mm and 2.7 mm. As illustrated in FIG. 7, it can be seen that as the diameter decreases, that is, as the region is closer to the center point P, an error from the target wavelength decreases. In contrast, it can be seen that as the diameter increases, the wavelength distribution becomes broad.

Figure 8:
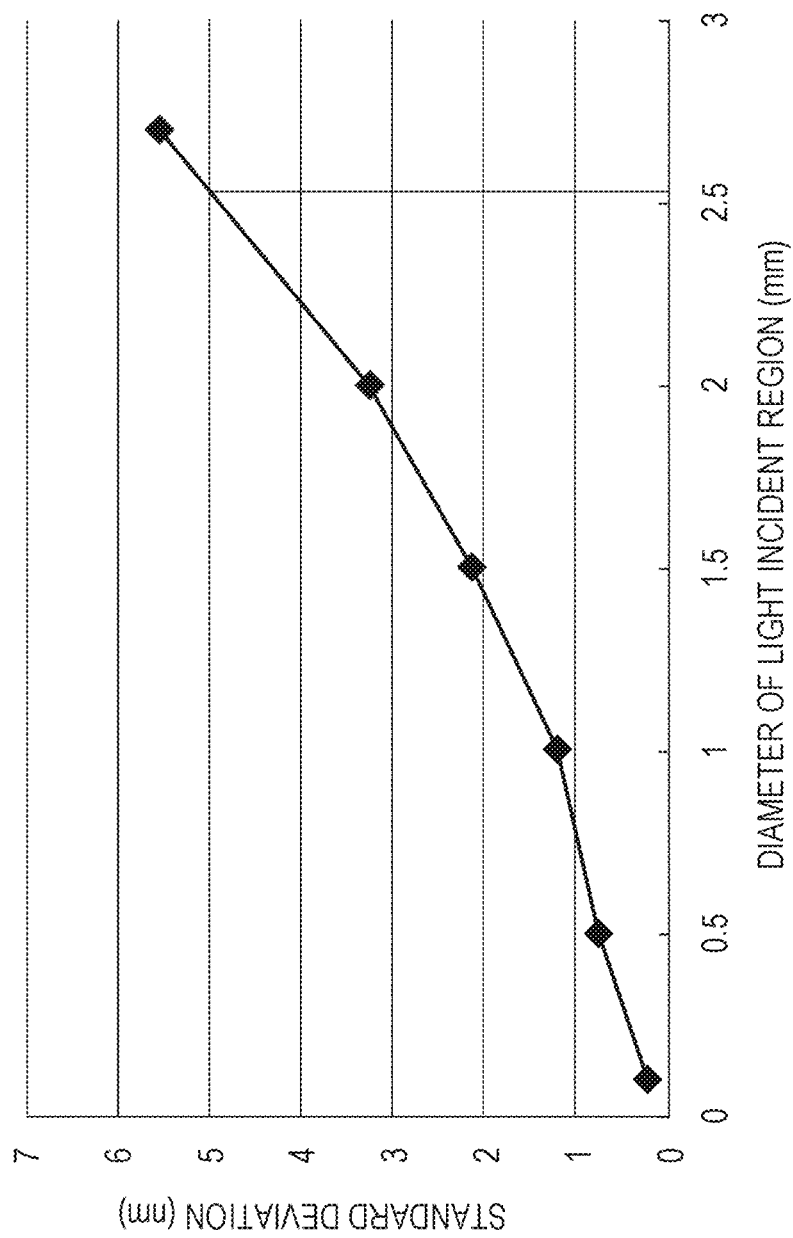
FIG. 8 is a graph showing an example of the diameter of the light incident region and a standard deviation of the wavelengths of the illumination light.

FIG. 8 is a graph representing a relationship between six different diameters represented in FIG. 7 and a standard deviation of measured wavelengths.

For example, when an allowable value of the standard deviation is set to 5 nm, and also when a diameter of the light incident region is set to 2.5 mm or less as represented in FIG. 8, it is possible to cause a value of the standard deviation to fall within a range of the allowable value. Accordingly, it is possible to set the diameter of the light incident region, that is, the diameter of the parallel light incident on the wavelength variable interference filter 5 to be equal to or smaller than the diameter of the effective region F2. In this case, when the wavelength of the illumination light is changed to a plurality of wavelengths, even though the wavelength is changed to a plurality of wavelengths having an interval of 10 nm, the wavelength of illumination light can be distinguished between wavelengths closest to each other.

Here, a dashed line of FIG. 6 corresponds to an outer periphery of the light incident region having a diameter of 2.5 mm. As represented in FIG. 6, a region inside the dashed line excludes a region corresponding to a wavelength of 410 nm and a region corresponding to a wavelength of 450 nm. Accordingly, when the diameter of the light incident region is set to 2.5 mm or less, it is possible to cause a maximum error between wavelengths to fall within a range of less than 40 nm, and it is possible to reduce a maximum value of the error.

It has been described in the example that the diameter of the facing region F1 between the reflection films 54 and 55 is 3.0 mm. However, even when the diameter is greater than 3.0 mm (for example, 3.5 mm, or 4.0 mm), the diameter of the light incident region is set to 2.5 mm, so that it is possible to cause the standard deviation of the wavelengths of the illumination light to fall within a range of 5 nm or less.

Effects of First Embodiment

The light from the light source section 111 is rendered into the parallel light having a diameter smaller than that of the facing region F1 of the pair of reflection films of the wavelength variable interference filter 5 by the condenser lens 112, and the parallel light is incident on the center of the facing region F1.

For example, when the aperture having the opening overlapped with the effective region F2 is provided on the light incident side of the wavelength variable interference filter 5, if the parallel light having a diameter greater than that of the effective region F2 is incident on the wavelength variable interference filter 5, the light incident outside the effective region F2 is blocked by the aperture. That is, some of the condensed light rays are blocked, and, thus, the amount of light of the light source device 10 is reduced.

In a plan view when viewed in a film thickness direction of the reflection films 54 and 55, bent portions or portions which have a non-uniform thickness are highly likely to exist in regions near the outer peripheries of the reflection films 54 and 55. Accordingly, compared to the centers of the reflection films, variation of the emission light is severed and the resolution is deteriorated in the regions near the outer peripheries of the reflection films 54 and 55. For this reason, when the aperture is not provided, if the light is incident on the entire facing region F1, the resolution of the emission light may be degraded.

In contrast, when the light from the light source section 111 is rendered into the parallel light having a size smaller than that of the facing region F1 and the parallel light is incident on the center of the facing region F1, it is possible to suppress a reduction in utilization efficiency of the light from the light source section 111, and it is possible to suppress a loss in the light amount. Further, it is possible to suppress a reduction in resolution of the emission light by causing the parallel light to be incident on the center of the facing region F1 while avoiding the region near the outer periphery of the facing region corresponding to the outer peripheries of the reflection films.

That is, it is possible to extract light having a predetermined wavelength from the light emitted from the light source section 111 with high efficiency and high resolution, and to use the extracted light as illumination light.

In the present embodiment, the parallel light is incident on the effective region F2 which is set inside the facing region F1 and causes the wavelength of the emission light to fall within a predetermined allowable error range of the target wavelength. In this case, it is possible to more reliably suppress a reduction in resolution of the emission light from the wavelength variable interference filter 5, and it is possible to output light having a desired target wavelength.

When the diameter of the parallel light is set to 2.5 mm or less, it is possible to suppress a value of the standard deviation representing the variation of the wavelength of the emission light from the wavelength variable interference filter 5 to be 5 nm or less. Accordingly, when illumination light having a plurality of different wavelengths is emitted, even when the plurality of wavelengths has an interval of 10 nm, the wavelength of the illumination light can be distinguished between wavelengths closest to each other, and a changing interval of the wavelength can be sufficiently decreased.

The ocular fundus observation apparatus includes the retreating unit 13 that retreats the wavelength variable interference filter 5 from the disposing position to the retreating position. Accordingly, it is possible to retreat the wavelength variable interference filter 5 to the retreating position, and it is possible to easily change the illumination light between dispersed light and undispersed light from the light source section 111.

Since the wavelength variable interference filter 5 is protected by the housing 610, it is possible to prevent foreign substances from adhering to the reflection films 54 and 55, and it is possible to protect the wavelength variable interference filter 5 by an external factor such as impacts.

The wavelength variable interference filter 5 may be directly provided in the light source device 10. It may be difficult to directly provide the wavelength variable interference filter 5 in the light source device 10 due to a complicated configuration. In the present embodiment, it is possible to easily provide the wavelength variable interference filter 5 even in such a light source device 10.

Second Embodiment

In the first embodiment, the optical filter device 600, the collimator 113 and the magnifying lens 114 are separately fixed. In contrast, in a second embodiment, the collimator 113 and the magnifying lens 114 are provided at the base 620 constituting the housing of the optical filter device. In the following description, a difference with the first embodiment will be primarily described, and description for the same configurations as those of the first embodiment will be omitted or simplified.

Figure 9:
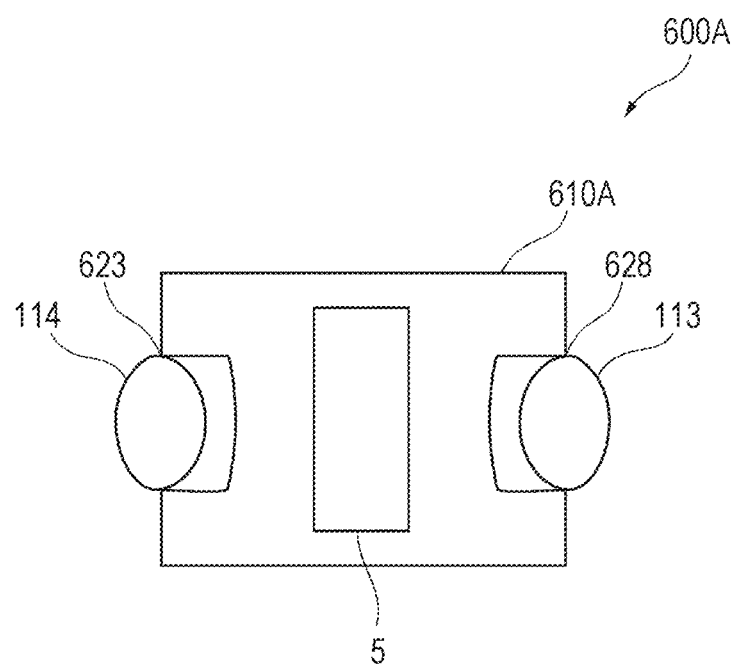
FIG. 9 is a diagram illustrating a schematic configuration of an optical filter device of a second embodiment.

FIG. 9 is a schematic diagram of an optical filter device of the second embodiment.

As shown in FIG. 9, an optical filter device 600A includes a housing 610A, and the wavelength variable interference filter 5 stored within the housing 610A. The collimator 113 and the magnifying lens 114 are provided at the housing 610. Specifically, the collimator 113 is provided at the window 628 on the light incident side of the housing 610A, and the magnifying lens 114 is provided at the opening 623 on the light emission side.

When the collimator 113 and the magnifying lens 114 are provided at the housing 610A, the collimator 113 and the magnifying lens 114 may be stored in the housing, and the housing may be fixed to the base 620. The collimator 113 and the magnifying lens 114 may be directly fixed to the base 620 through an adhesive.

Figure 10:
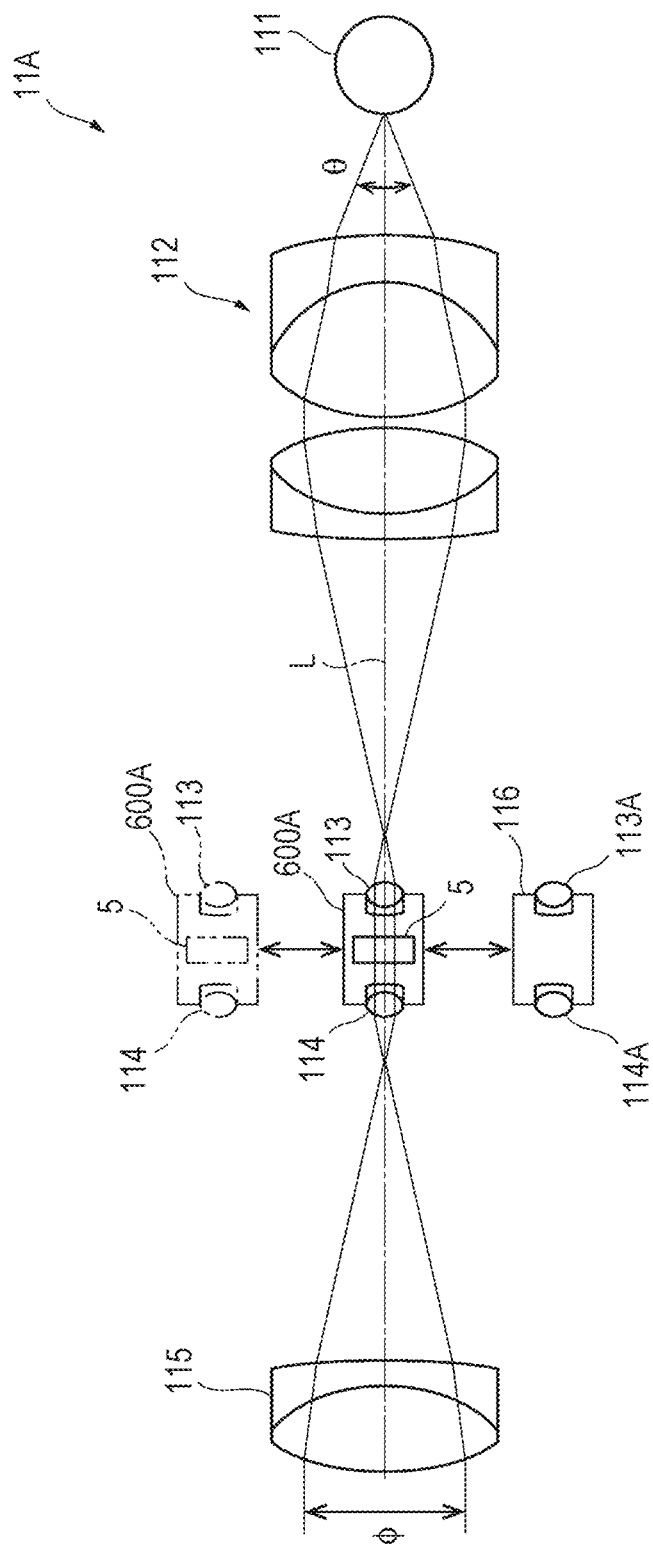
FIG. 10 is a diagram illustrating a schematic configuration of a light source unit of the second embodiment.

FIG. 10 is a schematic diagram of a light source unit of the second embodiment.

As shown in FIG. 10, in a light source unit 11A, the optical filter device 600A is disposed to be retreated from the optical path L by the retreating unit 13.

The light source unit 11A includes a second collimator 113A and a second magnifying lens 114A. The second collimator 113A and the second magnifying lens 114A are integrally held by the holding member 116. The second collimator 113A and the second magnifying lens 114A have the same optical characteristics as those of the collimator 113 and the magnifying lens 114. A relative positional relationship between the second collimator 113A and the second magnifying lens 114A is set to be the same as that between the collimator 113 and the magnifying lens 114.

In the second embodiment, the retreating unit 13 retreats the optical filter device 600A that includes the collimator 113 and the magnifying lens 114 in response to the retreating instruction. In this case, the retreating unit 13 moves the second collimator 113A and the second magnifying lens 114 held by the holding member 116 such that the second collimator 113A and the second magnifying lens 114A are arranged in positions where the collimator 113 and the magnifying lens 114 are arranged.

Effects of Second Embodiment

In the second embodiment, the collimator 113 is provided at the window 628 of the base 620 of the housing 610A constituting the optical filter device 600A, and the magnifying lens 114 is provided at the opening 623. With such a configuration, when the retreating unit 13 retreats the housing 610A together with the wavelength variable interference filter 5, the collimator 113 and the magnifying lens 114 are integrally moved. Accordingly, it is possible to suppress changes in positions between the wavelength variable interference filter 5 and the collimator 113 and between the wavelength variable interference filter and the magnifying lens 114 due to the movement of the wavelength variable interference filter 5.

The light source unit 11A includes the second collimator 113A and the second magnifying lens 114A that have the optical characteristics corresponding to the collimator 113 and the magnifying lens 114 and are arranged with the same positional relationship as that between the collimator and the magnifying lens. When the collimator 113 and the magnifying lens 114 are retreated, the second collimator 113A and the second magnifying lens 114A are arranged in the positions where the collimator 113 and the magnifying lens 114 are arranged. Accordingly, even when the collimator 113 and the magnifying lens 114 are retreated together with the optical filter device 600A, since the second collimator 113A and the second magnifying lens 114A are arranged in the disposing position, it is possible to focus the light from the light source section 111 on the ocular fundus X.

Other Embodiments

The present invention is not limited to the aforementioned embodiments, and changes and modifications are incorporated in the present invention within a range capable of achieving the advantage of some aspects of the present invention.

In the above-described embodiments, although the ocular fundus observation apparatus 1 has been described as an observation apparatus of the present invention, for example, the present invention is not limited thereto. For example, the present invention is applicable to various apparatuses using a light source device such as a microscope that emits illumination light having a predetermined wavelength.

Although it has been described in the aforementioned embodiments that the observation image corresponding to the wavelength of the illumination light is captured by the capturing element 24, an optical spectrum of the observation target may be measured. In this case, the control device 40 changes the driving voltage applied to the wavelength variable interference filter 5 in sequence. Accordingly, the wavelength of the illumination light applied to the observation target is changed in sequence, and is received by the capturing element 24. The control device 40 obtains light amounts of light rays having the respective wavelengths, and calculates the optical spectrum of the reflection light from the observation target.

In the aforementioned embodiments, although it has been described that the observation image can be captured by providing the optical device 20, the display unit 31 and the capturing element 24 as the observation unit, the present invention is not limited thereto. For example, an eyepiece may be provided as the observation unit instead of the capturing element 24, and, thus, the observation target can be observed with the naked eye.

In the second embodiment, although it has been described that the collimator 113 and the magnifying lens 114 are provided at the optical filter device 600A, the present invention is not limited thereto. For example, the wavelength variable interference filter 5 (the optical filter device 600), the collimator 113 and the magnifying lens 114 may be integrally held by the holding member. The collimator 113 and the magnifying lens 114 may be stored in a housing, and the housing may be fixed to the optical filter device 600. The collimator 113 and the magnifying lens 114 may be directly fixed to the optical filter device 600 through an adhesive. With such a configuration, the wavelength variable interference filter 5, the collimator 113 and the magnifying lens 114 can also be retreated to the retreating position while maintaining the relative positional relationship therebetween.

Although both of the collimator 113 and the magnifying lens 114 are integrally fixed to the wavelength variable interference filter 5, the present invention is not limited thereto. Any one of the collimator 113 and the magnifying lens 114 may be fixed to the wavelength variable interference filter.

In the second embodiment, although it has been described that when the collimator 113 and the magnifying lens 114 are arranged in the retreating position, the second collimator 113A and the second magnifying lens 114A with which the collimator 113 and the magnifying lens 114 are replaced are included, the present invention is not limited thereto. For example, instead of the second collimator 113A and the second magnifying lens 114A, one optical element equivalent to the collimator 113 and the magnifying lens 114 may be provided.

In the aforementioned embodiments, although the electrostatic actuator 56 is provided as a gap changing unit, the present invention is not limited thereto. As the gap changing unit, a piezoelectric actuator that is expanded or contacted by controlling a voltage applied to the piezoelectric actuator and changes the gap between the reflection films may be used. Alternatively, an actuator using a pneumatic pressure, or a configuration in which a dielectric coil and a magnet are used and the gap between the reflection films is changed by magnetic force may be used as the gap changing unit.

In the aforementioned embodiments, the wavelength variable interference filter 5 in which the fixed substrate 51 and the movable substrate 52 are bonded to face each other, the fixed reflection film 54 is formed on the fixed substrate 51 and the movable reflection film 55 is formed on the movable substrate 52 is provided as a Fabry-Perot etalon, the present invention is not limited thereto.

For example, the fixed substrate 51 and the movable substrate 52 are not bonded, but a gap changing unit such as a piezoelectric element that changes the gap between the reflection films may be provided between these substrates.

The two substrates are provided, but the present invention is not limited thereto. For example, there may be used a wavelength variable interference filter in which two reflection films are laminated on one substrate with a sacrificial film formed therebetween, and the sacrificial film is removed through etching to form a gap.

In the above-described embodiments, although it has been described that the wavelength variable interference filter 5 is assembled to the light source device 10 while being stored in the housing 610, the present invention is not limited thereto. The wavelength variable interference filter 5 may be directly disposed at the light source device 10.

In the above-mentioned embodiments, the wavelength variable interference filter 5 in which the inter-reflection-film gap G1 can be changed has been described, but the present invention is not limited thereto. The wavelength variable interference filter 5 in which the size of the inter-reflection-film gap G1 is fixed may be provided.

Alternatively, a plurality of interference filters may be provided instead of the wavelength variable interference filter, and the interference filter may be selectively changed.

The specific configuration of the embodiments of the present invention can be appropriately changed into other structures within the range capable of achieving the advantage of some aspects of the present invention.

The entire disclosure of Japanese Patent Application No. 2014-014083 filed on Jan. 29, 2014 is expressly incorporated by reference herein.

What is claimed is:

1. A light source device comprising:
a light source unit;
a light condensing unit that condenses light from the light source unit, and renders the condensed light into parallel light having a predetermined diameter; and
an interference filter that has a pair of reflection films facing each other, and emits light having a wavelength depending on a gap dimension of the pair of reflection films among the parallel light rays,
wherein the predetermined diameter is smaller than a size of a facing region of the interference filter where the pair of reflection films faces each other.

2. The light source device according to claim 1, wherein the parallel light is incident on an effective region in the facing region of the interference filter where a wavelength of emission light falls within a predetermined allowable error range of a target wavelength depending on the gap dimension.

3. The light source device according to claim 1, wherein the predetermined diameter is equal to or less than 2.5 mm.

4. The light source device according to claim 1, further comprising:
a retreating unit that retreats the interference filter from an optical path of the parallel light.

5. The light source device according to claim 1, further comprising:
a housing that stores the interference filter, and has a window that transmits light incident on the interference filter,
wherein the light condensing unit has a collimator that emits the parallel light, and
the collimator is provided at the window.

6. An observation apparatus comprising:
a light source device that includes a light source unit, a light condensing unit which condenses light from the light source unit and renders the condensed light into parallel light having a predetermined diameter, and an interference filter which has a pair of reflection films facing each other and emits light having a wavelength depending on a gap dimension of the pair of reflection films among the parallel light rays, the predetermined diameter being smaller than a size of a facing region of the interference filter where the pair of reflection films faces each other;
an illumination optical system that guides the light emitted from the light source device to illuminate a target; and
an observation unit that observes light reflected from the target.

7. A light source comprising:
a light source unit that emits first light;
a light condensing unit that condenses the first light to a second light; and
an interference filter that has a first reflection film and a second reflection film facing to the first reflection film, a third light among the second light passing through the interference filter,
the second light being projected onto one of the first reflection film and the second reflection film as a projected light having an area, the area being smaller than a facing area of the first reflection film and the second reflection film.

8. The light source device of claim 4, wherein the retreating unit moves the interference filter into and out of alignment with an optical path of the parallel light.

9. The observation apparatus according to claim 6, further comprising a retreating unit that moves the interference filter into and out of alignment with an optical path of the parallel light.

10. The light source of claim 7, further comprising a retreating unit that moves the interference filter into and out of alignment with an optical path of the parallel light.

* * * * *